United States Patent
Gulbenkian et al.

[11] Patent Number: 5,155,221
[45] Date of Patent: Oct. 13, 1992

[54] PROCESS FOR THE PREPARATION OF 2-ALKYLTHIO-4-HYDRAZINO-5-FLUOROPYRIMIDINES

[75] Inventors: Aylin H. Gulbenkian, Walnut Creek; Timothy C. Johnson, Concord; Wilmonte A. Nasutavicus, Lafayette, all of Calif.

[73] Assignee: DowElanco, Indianapolis, Ind.

[21] Appl. No.: 847,506

[22] Filed: Mar. 6, 1992

[51] Int. Cl.$^5$ .......................................... C07D 239/47
[52] U.S. Cl. .................................................. 544/317
[58] Field of Search ......................................... 544/317

[56] References Cited

U.S. PATENT DOCUMENTS 3,040,026  6/1962  Duschinsky ..................... 260/211.5
5,010,195  4/1991  Van Heertum et al. ............ 544/263

Primary Examiner—John M. Ford
Attorney, Agent, or Firm—Craig E. Mixan

[57] ABSTRACT

2-Alkylthio-4-hydrazino-5-fluoropyrimidines can be prepared from 2,4-dichloro-5-fluoropyrimidine in good yield with high selectivity by treatment with 2 equivalents of alkyl mercaptan in the presence of base followed by treatment with hydrazine.

1 Claim, No Drawings

PROCESS FOR THE PREPARATION OF 2-ALKYLTHIO-4-HYDRAZINO-5-FLUOROPYRIMIDINES

FIELD OF THE INVENTION

The present invention concerns a process for the preparation of 2-alkylthio 4 hydrazino 5 fluoro pyrimidines from 2,4 dichloro 5 fluoropyrimidine. More particularly, the present invention concerns the initial conversion of 2,4 dichloro 5 fluoropyrimidine to 2,4 bis(alkylthio)-5-fluoropyrimidine followed by reaction with hydrazine to produce the desired 2 alkylthio 4 hydrazino 5 fluoropyrimidine.

BACKGROUND OF THE INVENTION

5-Alkoxy 8 fluoro-1,2,4 triazolo[1,5 c]pyrimidine 2 sulfonamides (I),

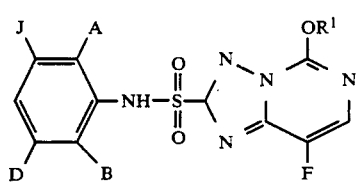

such as those described in EP 343,752 and U.S. Pat. No. 5,010,195, are valuable as herbicides. Compounds of this family are conveniently prepared from 2 alkylthio-4-hydrazino-5-fluoropyrimidines according to the following scheme.

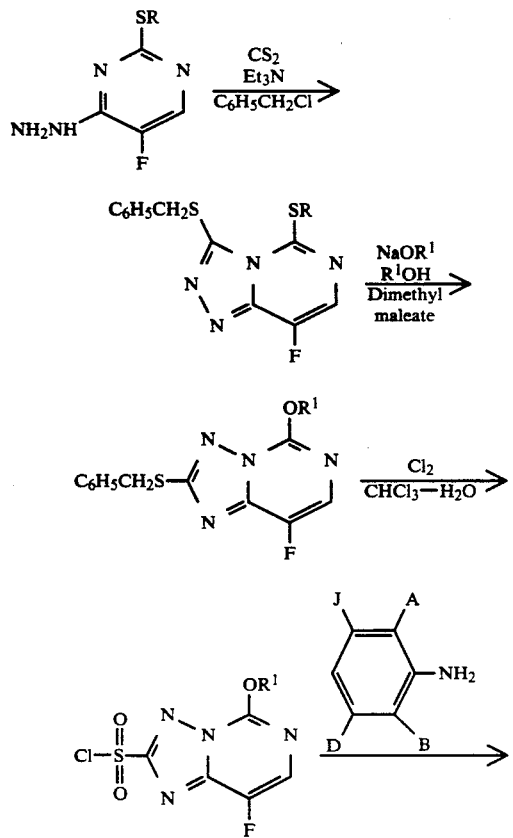

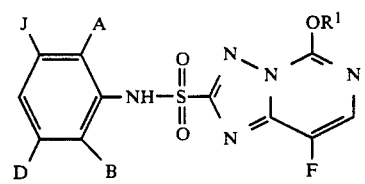

2-Alkylthio-4-hydrazino 5-fluoropyrimidines are themselves conveniently prepared from 2,4 dichloro 5-fluoropyrimidine. Since the chloro substituent in the 4-position proves to be more reactive than that in the 2 position, it is natural to first replace the chlorine in the 4 position with hydrazine and then to replace the chlorine in the 2-position with an alkyl mercaptan.

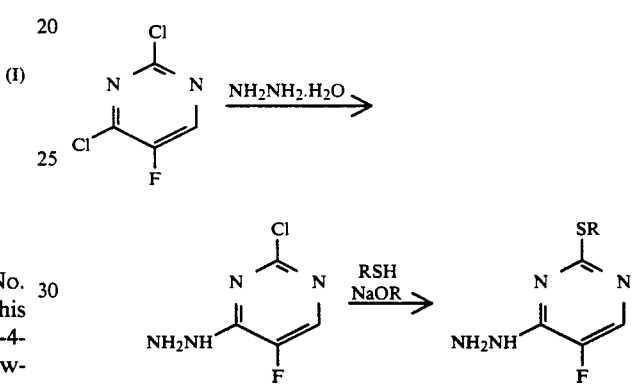

While this approach produces the desired 2-alkylthio-4-hydrazino-5-fluoropyrimidine, the yield is not exceptionally high. A similarly simple process that produces such hydrazinopyrimidines in good yield is thus highly desirable.

SUMMARY OF THE INVENTION

We have now found that 2 alkylthio-4 hydrazino -5 fluoropyrimidine can be prepared in good yield by first reacting 2,4-dichloro-5 fluoropyrimidine with about two equivalents of alkyl mercaptan followed by reaction with about one equivalent of hydrazine.

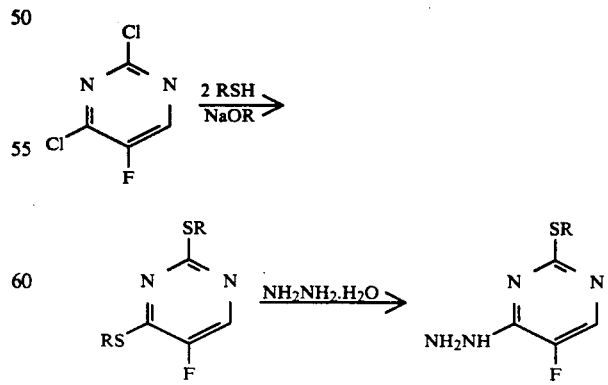

Therefore, the present invention concerns a process for the preparation of 2 alkylthio 4-hydrazino -5-fluoropyrimidines of formula (II)

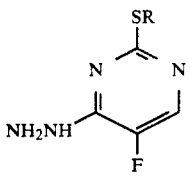

wherein R represents a straight or branched, saturated alkyl group of from 1 to 4 carbon atoms, which comprises the following steps:

(a) reacting 2,4-dichloro 5 fluoropyrimidine with about 2 equivalents of alkyl mercaptan in the presence of a base to give a 2,4 bis(alkylthio) 5 fluoropyrimidine of formula (III)

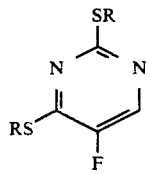

wherein R is as previously defined, and (b) reacting the 2,4-bis(alkylthio)-5-fluoro pyrimidine (III) with hydrazine to give the 2 alkylthio -4-hydrazino-5 fluoropyrimidine.

By initially reacting with the alkyl mercaptan rather than with hydrazine, the desired product is prepared with greater selectivity in surprisingly greater yield.

DETAILED DESCRIPTION OF THE INVENTION

As used herein, the term "alkyl" is meant to designate straight or branched, saturated alkyl groups of from 1 to 4 carbon atoms.

The starting material, 2,4-dichloro 5-fluoropyrimidine, is a known compound and may be prepared, for example, from 5-fluorouracil as described by G. J. Durr in *Synthetic Procedures in Nucleic Acid Chemistry*, W. W. Zorbach & R. S. Tipson (Eds.), page 92, or by R. Duschinsky in U.S. Pat. No. 3,040,026.

2.4 Bis(alkylthio)-5-fluoropyrimidines are prepared by contacting 2,4 dichloro 5-fluoropyrimidine with an alkyl mercaptan in the presence of a base. The reaction conditions employed are similar to those used for related exchange reactions of 2- and 4-chloropyrimidines: see. for example, *The Pyrimidines*, by D. J. Brown, from the series, *The Chemistry of Heterocyclic Compounds*, edited by Weissberger and Taylor. The reaction is usually conducted in nonaqueous media using at least stoichiometric ratios of reactants. Thus, for each equivalent of 2,4-dichloro 5 fluoropyrimidine, at least 2.0 equivalents of alkyl mercaptan are employed. While a stoichiometric excess of alkyl mercaptan might not be detrimental to the reaction, such an excess is not generally recommended unless adequate provisions are made for the recovery and recycle or for the destruction of so odorous a reagent.

Since it is desirable to convert the alkyl mercaptan completely into the corresponding thiolate anion, for each equivalent of alkyl mercaptan at least one equivalent of base is employed. Any base which is sufficiently strong to substantially convert alkyl mercaptan (RSH) to thiolate (RS$^\ominus$) and which is substantially less nucleophilic than thiolate is suitable. It is often most convenient to use the corresponding alkoxide (RO$^\ominus$) as the base. Similarly, while the reaction can be run in any inert organic solvent in which the reactants are at least partially soluble, it is often most convenient to conduct the reaction in an alcoholic solvent, particularly the alcohol corresponding to the preferred alkoxide base.

The reaction typically takes place between about −10° to about 60° C. Since the reaction is relatively exothermic, it is generally recommended that a solution of the thiolate be slowly added to a solution of 2,4-dichloro-5-fluoropyrimidine at an appropriate rate to control the reaction exotherm.

The first step of the process is usually conducted by placing the 2,4-dichloro-5-fluoropyrimidine and the solvent in a refrigerated vessel and then slowly adding a preformed mixture of alkyl mercaptan, base and solvent at a rate so as to maintain the temperature below ambient. After completion of the addition, the reaction mixture is mildly heated to finish the reaction and the desired 2,4-bis(alkylthio)-5-fluoropyrimidine is isolated by routine procedures such as precipitation/filtration or extraction.

2-Alkythio-4-hydrazino-5-fluoropyrimidines are prepared by contacting 2,4-bis(alkylthio)-5-fluoropyrimidines with hydrazine. The reaction is analogous to related amination reactions and is summarized in *The Pyrimidines*, by J. D. Brown, from the series, *The Chemistry of Heterocyclic Compounds*, edited by Weissberger and Taylor. Thus, hydrazine can typically be used in approximately equimolar quantities, but an excess is generally preferred in order to drive the reaction to completion. Non-nucleophilic, inorganic bases such as potassium carbonate, sodium bicarbonate, etc. can optionally be used to help maintain the displaced alkylmercaptan in the less odorous ionic form.

While the reaction can be run in any inert organic solvent in which the reactants are at least partially soluble, since hydrazine is usually used as the hydrate, it is often preferable to conduct the reaction in a water-miscible solvent. It is most convenient to employ the same alcoholic solvent used in the first step, in which case the overall process can be conducted without isolation of intermediates.

The reaction typically takes place from ambient to about 100° C. and is often conveniently carried out at the reflux temperature of the mixture.

The latter step of the process is usually conducted by placing the 2,4-bis(alkythio)-5-fluoropyrimidine, solvent and hydrazine in a vessel and heating until the reaction is complete. The 2-alkythio-4-hydrazino-5-fluoropyrimidine is isolated by routine procedures such as precipitation/filtration or extraction.

The following examples are presented to illustrate the invention and should not be construed as limiting the scope of the invention. Melting points are uncorrected.

EXAMPLE 1

Preparation of 2,4-Bis(methylthio)-5-fluoropyrimidine

A 2 liter (L) flask was charged with 2,4-dichloro-5-fluoropyrimidine (83.5 grams (g): 0.5 moles) and 200 milliliters (mL) of methanol and was chilled to a temperature of 0° to 5° C. Sodium methyl mercaptide was prepared from methyl mercaptan and sodium methoxide as a 25 percent solution in methanol and 280 g (1.0 moles) of this solution was added to the reactor at a rate to keep the temperature below 15° C. After the addition was complete, the reaction mixture was stirred at 35° C. for 1.5 hours (hr). The reaction mixture was concentrated to one half of its original volume under vacuum and was poured into 600 mL of ice-water. The pH was adjusted to 4 with dilute HCl and the solid product was isolated by filtration. After washing with water, the product was dried under vacuum to give 81.7g (86 percent yield) of 2,4-bis(methylthio)-5-fluoropyrimidine having a melting point of 41°–42° C.

EXAMPLE 2

Preparation of 2-Methylthio-4-hydrazino-5-fluoropyrimidine

A 1 liter (L) flask equipped with a condensor and thermometer was charged with 80g (0.42 moles) of 2,4-bis(methylthio)-5-fluoropyrimidine, 200 mL of ethanol and 105g (2.1 moles) of hydrazine hydrate. The reaction mixture was poured onto 350 mL of ice-water. The solid product was isolated by filtration. After washing with water, the product was dried under vacuum at 60° C. to give 62.8g (86 percent yield) of 2-methylthio-4-hydrazino-5-fluoropyrimidine having a melt point of 146°–147° C.

What is claimed is:

1. A process for the preparation of 2 alkyl thio 4 hydrazino 5 fluoropyrimidines of formula (II)

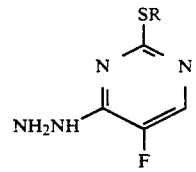

wherein R represents a straight or branched, saturated alkyl group of from 1 to 4 carbon atoms, which comprises the following steps:

(a) reacting 2.4 dichloro-5 fluoro pyrimidine with about 2 equivalents of alkyl mercaptan in the presence of a base to give a 2,4 bis(alkylthio)-5-fluoropyrimidine of formula (III)

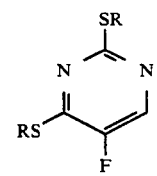

wherein R is as previously defined, and (b) reacting the 2,4 bis(alkylthio) 5 fluoro pyrimidine with hydrazine to give the 2 alkylthio 4-hydrazino 5 fluoropyrimidine.

* * * * *